US00PP34993P2

(12) United States Plant Patent
Leenaerts

(10) Patent No.: US PP34,993 P2
(45) Date of Patent: Feb. 21, 2023

(54) ***PHYSOCARPUS* PLANT NAMED 'LP1'**

(50) Latin Name: *Physocarpus opulifolius*
Varietal Denomination: LP1

(71) Applicant: Robert Johannes Marie Leenaerts, Achtmaal (NL)

(72) Inventor: Robert Johannes Marie Leenaerts, Achtmaal (NL)

(73) Assignee: LEENA BEHEER B.V., Achtmaal (NL)

( * ) Notice: Subject to any disclaimer, the term of this patent is extended or adjusted under 35 U.S.C. 154(b) by 0 days.

(21) Appl. No.: 17/582,213

(22) Filed: Jan. 24, 2022

(51) Int. Cl.
*A01H 6/74* (2018.01)
*A01H 5/02* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Penny J. Aguirre

(57) ABSTRACT

A new cultivar of *Physocarpus opulifolius* plant named 'LP1' that is characterized by its compact plant habit, its young foliage that is brown-red to orange-red in color and mature foliage that changes to orange in color, and its foliage that turns to a brownish color in autumn.

2 Drawing Sheets

Botanical classification: *Physocarpus opulifolius*.
Varietal denomination: 'LP1'.

CROSS REFERENCE TO RELATED APPLICATIONS

This application is related to a European plant breeders' rights application filed on Mar. 3, 2020, application No. 2020/0631, a Korean plant breeders' rights application filed on Nov. 30, 2020, application No. 201009, and a United Kingdom plant breeders' rights application filed on Jun. 14, 2021, application No. XU_30202100003152. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Physocarpus opulifolius* and will be referred to hereafter by its cultivar name, 'LP1'. 'LP1' represents a new cultivar of *Physocarpus*, a deciduous shrub grown for landscape use.

'LP1' was discovered August of 2016 by the Inventor as a chance seedling in a trial field in Achtmaal, The Netherlands. The field had been planted with seeds derived from open pollination of unpatented and unnamed proprietary seedlings from the Inventors breeding program. The parentage is therefore unknown.

Asexual propagation of the new cultivar was first accomplished by softwood stem cuttings by the Inventor in August of 2016 in Achtmaal, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and are determined to be the characteristics of the new cultivar.

These attributes in combination distinguish 'LP1' as a unique and distinct cultivar of *Physocarpus*.

1. 'LP1' exhibits a compact plant habit.
2. 'LP1' exhibits young foliage that is brown-red to orange-red in color and mature foliage that changes to orange in color.
3. 'LP1' exhibits foliage that turns to a brownish color in autumn.

'LP1' can be compared to the *Physocarpus opulifolius* cultivars 'Jefam' (U.S. Plant Pat. No. 23,177) and 'Chameleon' (not patented). Both 'Jefam' and 'Chameleon' are similar to 'LP1' in plant shape. 'Jefam' differs from 'LP1' in having spring foliage that is orange in color, summer and autumn foliage that is green in color, a taller plant height, and a less compact plant habit. 'Chameleon' differs from 'LP1' in having spring foliage that is irregularly variegated with deep brownish-red and yellow colors and summer foliage that is irregularly variegated with yellow and green colors.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Van Vilet New Plants, Leena Plant Boomkwekerijen, Vorzel Garden, Sp-garden, Prom, Langthorns plantery, Floral Daily (Neil Alcock), Plant2gardens, Visions Pictures, The National Gardening Association plant database, and Hortweek.

BRIEF DESCRIPTION OF THE DRAWINGS

The accompanying color photographs illustrate the overall appearance and distinct characteristics of the new *Physo-*

*carpus*. The photographs were taken of a plant 18 months in age as grown in a 13-cm container outdoors in Achtmaal, The Netherlands.

Figure 1:
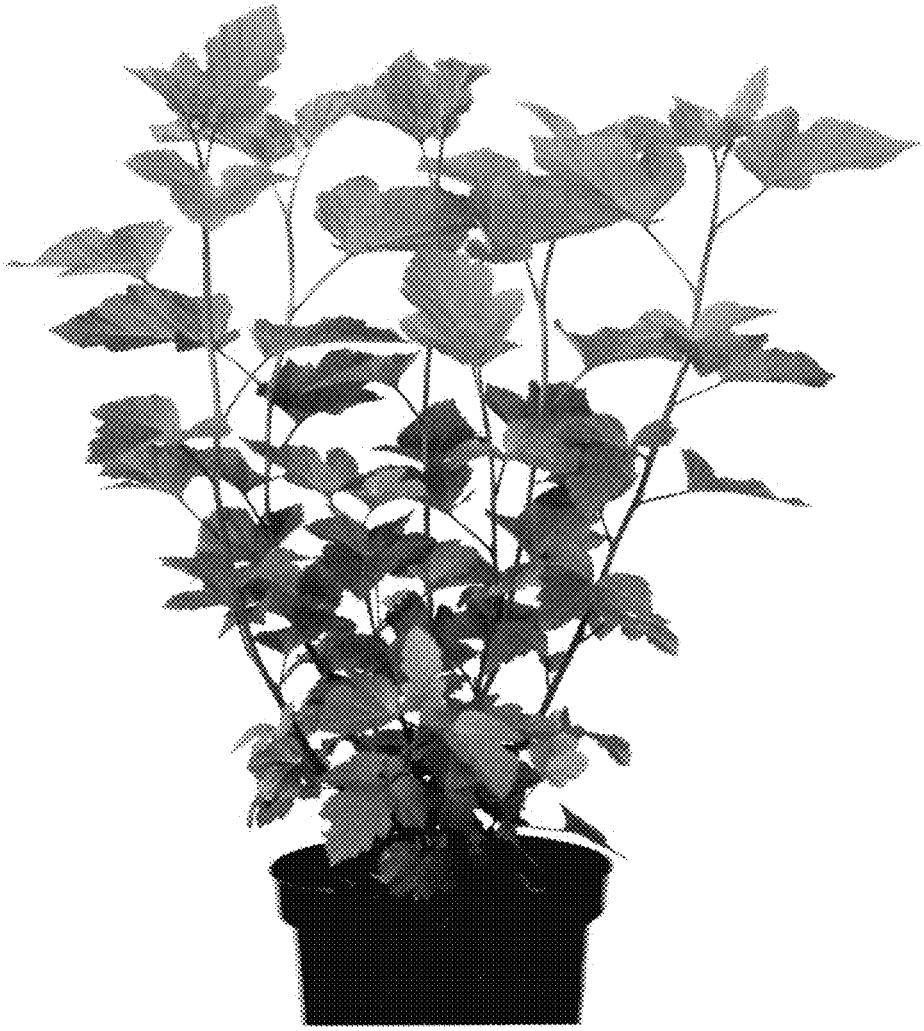

The photograph in FIG. 1 provides a side view of the plant habit of 'LP1'.

Figure 2:
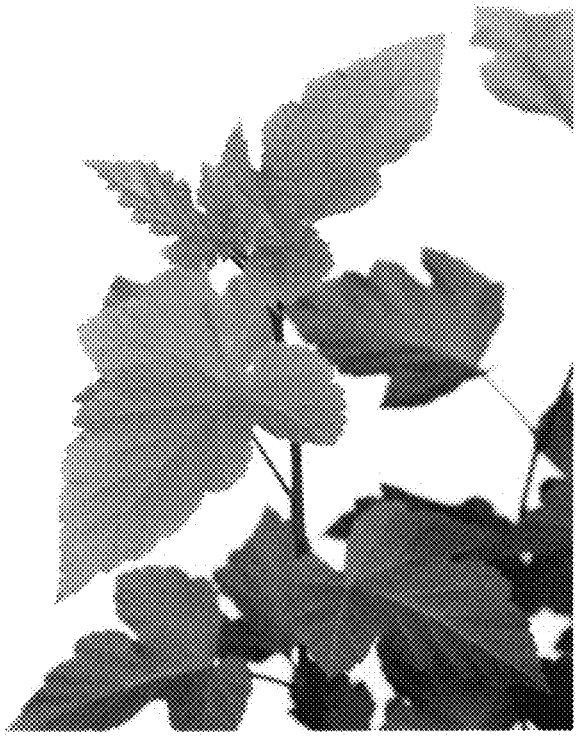

The photograph in FIG. 2 provides a close-up view of the young foliage of 'LP1'.

Figure 3:
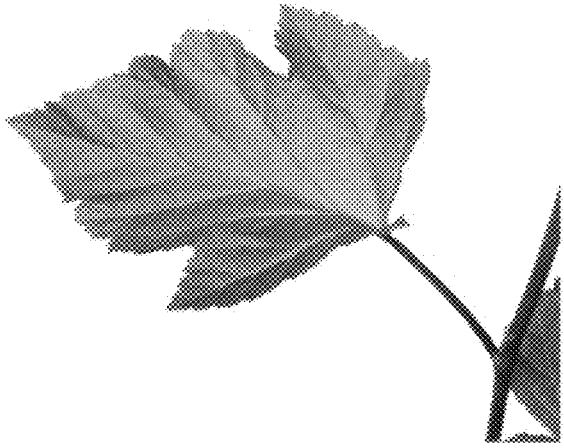

The photograph in FIG. 3 provides a close-up view of a mature leaf of 'LP1'.

The colors in the photographs are as close as possible with the digital photography and printing techniques utilized and the color codes in the detailed botanical description accurately describe the colors of the new *Physocarpus*.

BOTANICAL DESCRIPTION OF THE PLANT

The following is a detailed description of 18-month-old plants of the new cultivar as grown outdoors in a 13-cm containers in Achtmaal, The Netherlands. Phenotypic differences may be observed with variations in environmental, climatic, and cultural conditions. The color determination is in accordance with The 2015 Colour Chart of The Royal Horticultural Society, London, England, except where general color terms of ordinary dictionary significance are used.

General description:

*Plant type*.—Deciduous shrub.

*Plant habit*.—Compact.

*Plant shape*.—Broadly obovate.

*Height and spread*.—37.6 cm in height, 35.5 cm in width, a fully mature plant in the landscape reaches an average of 1.5 m in height and 1.25 m in width.

*Cold hardiness*.—At least to U.S.D.A. Zone 3.

*Diseases and pest resistance*.—No resistance or susceptibility to diseases or pests has been observed.

*Root description*.—Fibrous and fine.

*Propagation*.—Softwood stem cuttings.

*Root development*.—An average of 6 weeks to initiate roots and about 5 months to produce a fully rooted young plant.

*Growth rate*.—Moderate.

Branch description:

*Branch color*.—Young; 172A and 172B, maturing; 183B and 183C, old bark; a blend of 199C, N199B, N199C and 200C.

*Branch size*.—An average of 27.6 cm in length and 3 mm in diameter.

*Number of lateral branches*.—An average of 5 main branches, 9 secondary branches per plant.

*Branch surface*.—Slightly glossy, mature bark finely barked and exfoliating.

*Shape*.—Young stems are angled with 3 sides, older stems round.

*Internode length*.—An average 3.4 cm.

*Branching habit*.—Freely branched, average angle of 30°.

*Branch strength*.—Strong.

Foliage description:

*Leaf shape*.—Broad ovate to cordate in outline, three-lobed.

*Leaf aspect*.—Slightly carinate to slightly convexed.

*Leaf division*.—Simple.

*Leaf base*.—Cordate, lobes free to slightly overlapping.

*Leaf apex*.—Acute.

*Leaf venation*.—Pinnate, color; upper surface N144C, lower surface 148A.

*Leaf margin*.—Serrate.

*Leaf attachment*.—Petiolate.

*Leaf arrangement*.—Alternate.

*Leaf surface*.—Both surfaces smooth, non-rugose, matte with small tufts of short hairs in the vein of the axils of the main and secondary veins an average of 5 mm in length and 160D in color.

*Leaf size*.—An average of 7.8 cm in length and 6.8 cm in width.

*Leaf number*.—Average of 9 per lateral branch.

*Leaf color*.—Young foliage upper surface 173A, lower surface 174B, top 199C, mature foliage upper surface 146C, tinged 177A and 200C, mature foliage lower surface 147C, tinged 195A, fall color upper and lower surface 177A and 200A.

*Petiole*.—An average of 2.1 cm in length, 1.2 mm in width, strong, both sides smooth, glabrous, moderately glossy, colors; young leaves upper surface 180A, mature leaves upper surface 183B, young leaves lower surface 180B, mature leaves lower surface 178A to 178B.

*Stipules*.—2 leafy stipules present at the proximal end of each petiole, narrow ovate to elliptical in shape, acute to apiculate tip, narrow cuneate base, an average of 6 mm in length and 2.5 mm in width, margins are irregularily serrate, color; upper surface 180B, margins 148A, lower surface 180C, margins 146A to 146B.

Flower description:

*Flower type*.—Small rotate flowers arranged in spherical corymb, similar to parents and typical of the species *Physocarpus opulifolius*.

*Flower fragrance*.—None.

*Flower lastingness*.—Average of one week, self-cleaning.

*Flower bud description*.—Ovate in shape, average of 4 mm in length and 2 mm in diameter, surface is smooth, matte and glabrous, 144A to 144B in color.

*Flower quantity*.—Average of 25 flowers per inflorescence, 250 flowers per plant, up to 1000 flowers and flower buds per plant.

*Inflorescence size*.—Average of 4.5 cm in height and diameter.

*Flower size*.—Average of 6 mm in height, diameter, and depth.

*Peduncles*.—Average of 3 cm in length and 1 mm in diameter, moderately strong, held in a straight vertical angle, 144A in color, surface is glabrous, matte, and smooth.

*Pedicels*.—Average of 2.1 cm in length and 0.5 mm in diameter, moderately strong, held in an average angle of 25° to vertical, 144B in color, surface is glabrous, matte, and smooth.

*Petal description*.—5, broadly ovate in shape, margin is entire, short apiculate apex, 3 mm in length, 2 mm in width, upper and lower surface glabrous, velvety, matte, and non-rugose, color: when opening upper surface NN155D, strongly tinged 65B, when opening lower surface NN155D, tinged 65B to 65C, when fully open upper and lower surface NN155D, tinged 65D.

*Calyx*.—Rotate, average of 4 mm in length, 6 mm in diameter.

*Sepal description*.—5, rotate, cup-shaped, entire margins, acute apex, broadly cuneate base, an average of 4 mm in length and 1.5 mm in width, both surfaces are matte, upper surface moderately pubescent covered with short adpressed hairs an average of 0.2 mm in length, too small to measure color, color: when opening and fully open upper surface 138D, when opening and fully open lower surface 144B.

Reproductive organs:

*Gynoecium*.—Pistils; 5, 3.5 cm in length, stigmas; club-shaped, 0.5 mm in length and diameter, 151D in color, styles; 3 mm in length, 150D in color, ovary; 145C in color.

*Androecium*.—Stamens; 25, anthers; double kidney-shaped, 0.3 mm in length and width, 159B to 159C, filaments; 2 mm in length, 157D in color, pollen; none.

*Fruit and seed*.—None produced.

It is claimed:

1. A new and distinct cultivar of *Physocarpus* plant named 'LP1' substantially as herein illustrated and described.

* * * * *